(12) United States Patent
Liu

(10) Patent No.: US 9,854,842 B2
(45) Date of Patent: Jan. 2, 2018

(54) BATTERY ASSEMBLY AND ATOMIZING ASSEMBLY OF ELECTRONIC CIGARETTE, AND ELECTRONIC CIGARETTE

(71) Applicant: Qiuming Liu, Shenzhen (CN)

(72) Inventor: Qiuming Liu, Shenzhen (CN)

(73) Assignee: HUIZHOU KIMREE TECHNOLOGY CO., LTD. SHENZHEN BRANCH, Guangdong (CN)

( * ) Notice: Subject to any disclaimer, the term of this patent is extended or adjusted under 35 U.S.C. 154(b) by 7 days.

(21) Appl. No.: 14/119,007

(22) PCT Filed: Sep. 27, 2013

(86) PCT No.: PCT/CN2013/084420
§ 371 (c)(1),
(2) Date: Nov. 20, 2013

(87) PCT Pub. No.: WO2015/035674
PCT Pub. Date: Mar. 19, 2015

(65) Prior Publication Data
US 2016/0278431 A1    Sep. 29, 2016

(30) Foreign Application Priority Data
Sep. 13, 2013  (CN) ..................... 2013 2 0571427 U

(51) Int. Cl.
*A24F 47/00*  (2006.01)
*G06K 9/32*   (2006.01)
(Continued)

(52) U.S. Cl.
CPC ........... *A24F 47/008* (2013.01); *A61M 15/06* (2013.01); *G06K 9/325* (2013.01); *G06K 9/3241* (2013.01);
(Continued)

(58) Field of Classification Search
CPC ..................................................... A24F 47/008
See application file for complete search history.

(56) References Cited

U.S. PATENT DOCUMENTS

2010/0163063 A1\* 7/2010 Fernando ............. A24F 47/008
                                                  131/184.1
2011/0226236 A1   9/2011 Buchberger
(Continued)

FOREIGN PATENT DOCUMENTS

CN          2870485 Y    2/2007
CN        201054977 Y    5/2008
(Continued)

OTHER PUBLICATIONS

CN 203192003 Translation; Teng Yuanzhi; Sep. 2013.\*
Extended European Search Report dated Jun. 16, 2017 for European application No. 13893634.9.

*Primary Examiner* — Eric Yaary
(74) *Attorney, Agent, or Firm* — Ohlandt, Greeley, Ruggiero & Perle, LLP

(57) ABSTRACT

The present application provides a battery assembly of an electronic cigarette which is adapted to form an electronic cigarette in combination with an atomizing assembly. An image identification device includes an image sensor and a microprocessor. The microprocessor matches an identifier to be identified collected by the image sensor with a preset identifier, and if the identifier to be identified matches with the preset identifier, the microprocessor controls a circuit between the battery assembly and the atomizing assembly to turn on, thus the electronic cigarette can work normally. That is, the electronic cigarette has an identification function that it can be normally used only when the battery assembly and the atomizing assembly of the electronic cigarette are matched, thereby avoiding damage to the connectors of the electronic cigarette caused by mismatching. In addition, the
(Continued)

present application may further avoid the user having a poor experience due to use of the conventional battery assembly and atomizing assembly in any combination, mixed use of tobacco tars having different flavors, and mixed use of the battery assembly and the atomizing assembly from different manufacturers. Thus, the present application may facilitate the recognition of the user of the manufactures and brands, and is more beneficial for the user to quit smoking.

8 Claims, 7 Drawing Sheets

(51) Int. Cl.
| | | |
|---|---|---|
| *G06K 9/62* | (2006.01) | |
| *H02J 7/00* | (2006.01) | |
| *H04N 5/374* | (2011.01) | |
| *A61M 15/06* | (2006.01) | |

(52) U.S. Cl.
CPC .......... *G06K 9/6215* (2013.01); *H02J 7/0052* (2013.01); *H04N 5/374* (2013.01); *A61M 2205/6063* (2013.01)

(56) References Cited

U.S. PATENT DOCUMENTS

| 2014/0060524 A1 | 3/2014 | Liu | |
|---|---|---|---|
| 2014/0096782 A1* | 4/2014 | Ampolini | A24F 47/008 131/328 |
| 2014/0299141 A1* | 10/2014 | Flick | H05B 1/0202 131/329 |

FOREIGN PATENT DOCUMENTS

| CN | 201869778 U | | 6/2011 |
|---|---|---|---|
| CN | 202618275 U | | 12/2012 |
| CN | 203192003 U | * | 9/2013 |
| WO | 199920940 A1 | | 4/1999 |

* cited by examiner

BATTERY ASSEMBLY AND ATOMIZING ASSEMBLY OF ELECTRONIC CIGARETTE, AND ELECTRONIC CIGARETTE

CROSS-REFERENCED APPLICATIONS

This application is the national phase of International Application No. PCT/CN2013/084420, titled "BATTERY ASSEMBLY AND ATOMIZING ASSEMBLY OF ELECTRONIC CIGARETTE, AND ELECTRONIC CIGARETTE", filed on Sep. 27, 2013, which claims the benefit of priority to Chinese patent application No. 201320571427.8, titled "BATTERY ASSEMBLY AND ATOMIZING ASSEMBLY OF ELECTRONIC CIGARETTE, AND ELECTRONIC CIGARETTE" and filed with the Chinese State Intellectual Property Office on Sep. 13, 2013, the entire disclosure of which is incorporated herein by reference.

BACKGROUND

1. Field of the Disclosure

The present application relates to the technical field of image identification, and particularly to a battery assembly and an atomizing assembly of an electronic cigarette, and an electronic cigarette.

2. Discussion of the Background Art

A conventional electronic cigarette mainly includes a battery assembly and an atomizing assembly, the structure of which is shown in FIG. 1. The battery assembly includes an end cap 11, a microphone controller 12, a microphone seat 13, a battery 14, a battery sleeve 15, a lower electrode 16, an electrode fixing seat 17 and a connecting seat 18. The atomizing assembly includes a connector 20, an upper electrode 21, an upper insulating ring 22, an atomizing seat 23, an atomizing device 24, a PVC fiberglass sleeving 25, a tar storage cotton 26, an atomizing sleeve 27 and a mouthpiece cover 28.

In conjunction with FIG. 1, the electronic cigarette can work normally by connecting the connecting seat 18 in the battery assembly to the connector 20 in the atomizing assembly. The inventor found that, conventional electronic cigarettes may be used in combination as long as connectors of the battery assembly and the atomizing assembly can be connected, irrespective of brands of the electronic cigarettes. Thus, when the battery assembly and the atomizing assembly, which are not matched, are used in combination, the connectors of the electronic cigarettes may be damaged, which may further shorten the service life of the electronic cigarettes. Since a conventional battery assembly and atomizing assembly can be used in any combination, it is apt to cause the mixed use of tobacco tars having different flavors and the mixed use of the battery assembly and the atomizing assembly from different manufacturers, which may cause a poor user experience, hinders a user from knowing about the manufacturers and the brands, and is not beneficial for the user to quit smoking.

SUMMARY

In view of this, the present application provides a battery assembly and an atomizing assembly of an electronic cigarette, and an electronic cigarette, so as to effectively solve the problem in the prior art that connectors of the electronic cigarettes may be damaged when the battery assembly and the atomizing assembly, which are not matched, are used in combination.

In order to achieve the above object, the present application provides the following technical solutions.

A battery assembly of an electronic cigarette, which is adapted to form an electronic cigarette in combination with an atomizing assembly, wherein the battery assembly includes an image identification device configured to identify an identifier to be identified which is arranged on an atomizer, and the image identification device includes:

an image sensor configured to collect the identifier to be identified; and a microprocessor connected to the image sensor, and in a case that the microprocessor determines that the identifier to be identified matches with a preset identifier, the microprocessor is configured to control a circuit between the battery assembly and the atomizing assembly to turn on so as to enable the electronic cigarette to work normally.

Preferably, the image sensor is an infrared sensor, a photosensitive camera, an ultrasonic imager, a thermal imaging sensor or a magnetic induction imager.

Preferably, the image sensor is an OID code identification chip or an SPCA563B image identification chip.

Preferably, the battery assembly further includes:

a power management circuit arranged between a battery and the microprocessor in the battery assembly and configured to manage an external power supply to charge the battery.

Preferably, the battery assembly further includes:

a prompting device electrically connected to the microprocessor and configured to display an identification result from the microprocessor, wherein the prompting device is an alarm or an indicator light.

An atomizing assembly of an electronic cigarette is provided, wherein an identifier to be identified by a battery assembly is arranged on a portion, close to the battery assembly, of the atomizing assembly.

Preferably, the identifier to be identified is a trademark of the electronic cigarette.

Preferably, the identifier to be identified is a pattern or a text of a planar or a three-dimensional shape.

Preferably, the atomizing assembly is provided with an upper electrode adapted to electrically connect to the battery assembly, the upper electrode is provided with an outer electrode and an inner electrode which are sleevedly engaged, and the identifier to be identified is arranged on the inner electrode.

An electronic cigarette includes a battery assembly and an atomizing assembly, wherein the battery assembly is any one of the battery assemblies described above, and the atomizing assembly is any one of the atomizing assemblies described above.

It can be known from the above technical solutions that, compared with the prior art, the present application provides a battery assembly of an electronic cigarette which is adapted to form an electronic cigarette in combination with an atomizing assembly. An image identification device includes an image sensor and a microprocessor. The microprocessor matches an identifier to be identified collected by the image sensor with a preset identifier, and if the identifier to be identified matches with the preset identifier, the microprocessor controls a circuit between the battery assembly and the atomizing assembly to turn on, thus the electronic cigarette can work normally. That is, the electronic cigarette has an identification function that it can be normally used only when the battery assembly and the atomizing assembly of the electronic cigarette are matched, thereby avoiding damage to the connectors of the electronic cigarette caused by mismatching. In addition, the present application may further avoid the user having a poor experience due to use of the conventional battery assembly and atomizing assembly in any combination, mixed use of tobacco tars having different flavors, and mixed use of the battery assembly and the atomizing assembly from different manufacturers. Thus, the present application may facilitate the recognition of the user of the manufactures and brands, and is more beneficial for the user to quit smoking.

BRIEF DESCRIPTION OF THE DRAWINGS

For more clearly illustrating embodiments of the present application or the technical solution in the prior art, drawings referred to describe the embodiments or the prior art will be briefly described hereinafter. Apparently, the drawings in the following description are only several embodiments of the present application, and for the person skilled in the art other drawings may be obtained based on these drawings without any creative efforts.

DETAILED DESCRIPTION OF THE PREFERRED EMBODIMENT

The present application provides a battery assembly and an atomizing assembly of an electronic cigarette, and an electronic cigarette, wherein the electronic cigarette has an image identification function to ensure that the electronic cigarette can be normally used only when the battery assembly and the atomizing assembly are matched, thereby avoiding damage to connectors of the electronic cigarette caused by mismatching, and avoiding unnecessary troubles caused by interchange between connectors of electronic cigarettes in different brands.

The technical solutions in the embodiments of the present application will be described clearly and completely hereinafter in conjunction with the drawings in the embodiments of the present application. Apparently, the described embodiments are only a part of the embodiments of the present application, rather than all embodiments. Based on the embodiments in the present application, all of other embodiments, made by the person skilled in the art without any creative efforts, fall into the protection scope of the present application.

First Embodiment

Figure 1:
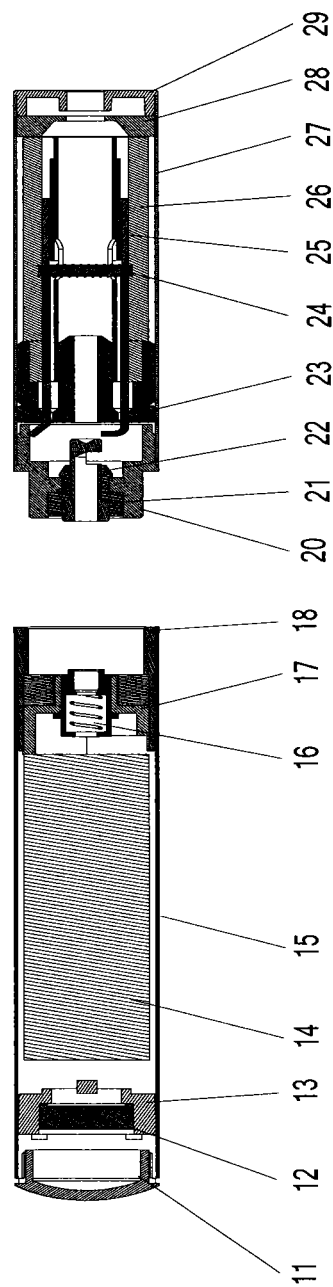
FIG. 1 is a schematic view showing the structure of an electronic cigarette in the prior art.
Figure 2:
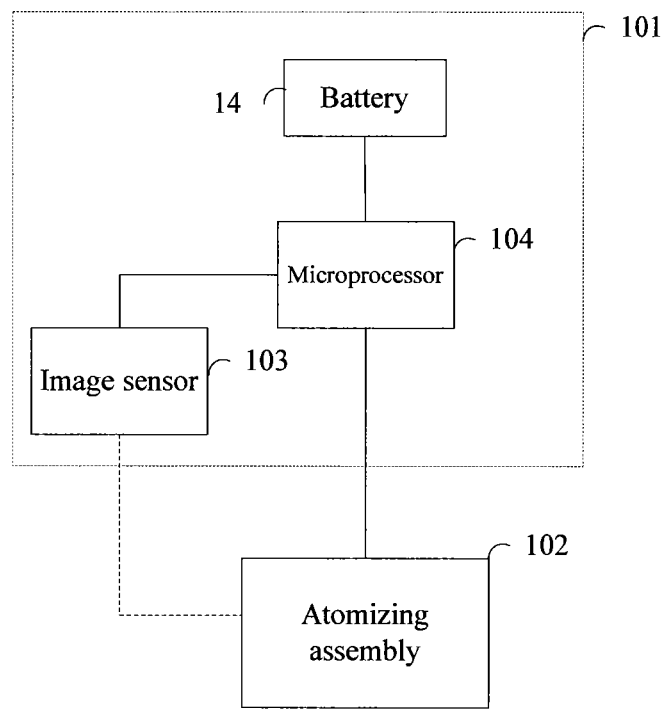
FIG. 2 is a functional block diagram of a battery assembly of an electronic cigarette according to a first embodiment of the present application.

Referring to FIG. 2, a battery assembly 101 of an electronic cigarette according to an embodiment of the present application is adapted to form an electronic cigarette in combination with an atomizing assembly 102. The battery assembly 101 includes an image identification device for identifying an identifier to be identified which is arranged on an atomizer, and the image identification device includes an image sensor 103 and a microprocessor 104.

The image sensor 103 collects the identifier to be identified on the atomizing assembly 102, and sends a collected image to the microprocessor 104. Then, the microprocessor 104 determines whether the identifier to be identified matches with a preset identifier, and when the identifier to be identified matches with the preset identifier, the microprocessor controls a circuit between the battery assembly and the atomizing assembly to turn on, and at this time, the electronic cigarette can work normally. When the identifier to be identified does not match with the preset identifier, the microprocessor controls the circuit between the battery assembly and the atomizing assembly to turn off, and at this time, the electronic cigarette cannot work normally since it is powered off.

As can be seen that, the electronic cigarette has an identification function and can be normally used only when the battery assembly and the atomizing assembly of the electronic cigarette are matched, thereby avoiding damage to connectors of the electronic cigarette caused by mismatching. In addition, since the electronic cigarette is provided with the image identification device, the present application has many additional advantages, for example, it is able to query some performances of the product, information of the manufacturer, protection between products, functional setting and cooperation between products, and realize child protection (preventing a child from smoking the cigarette) by means of image identification.

Second Embodiment

Figure 3:
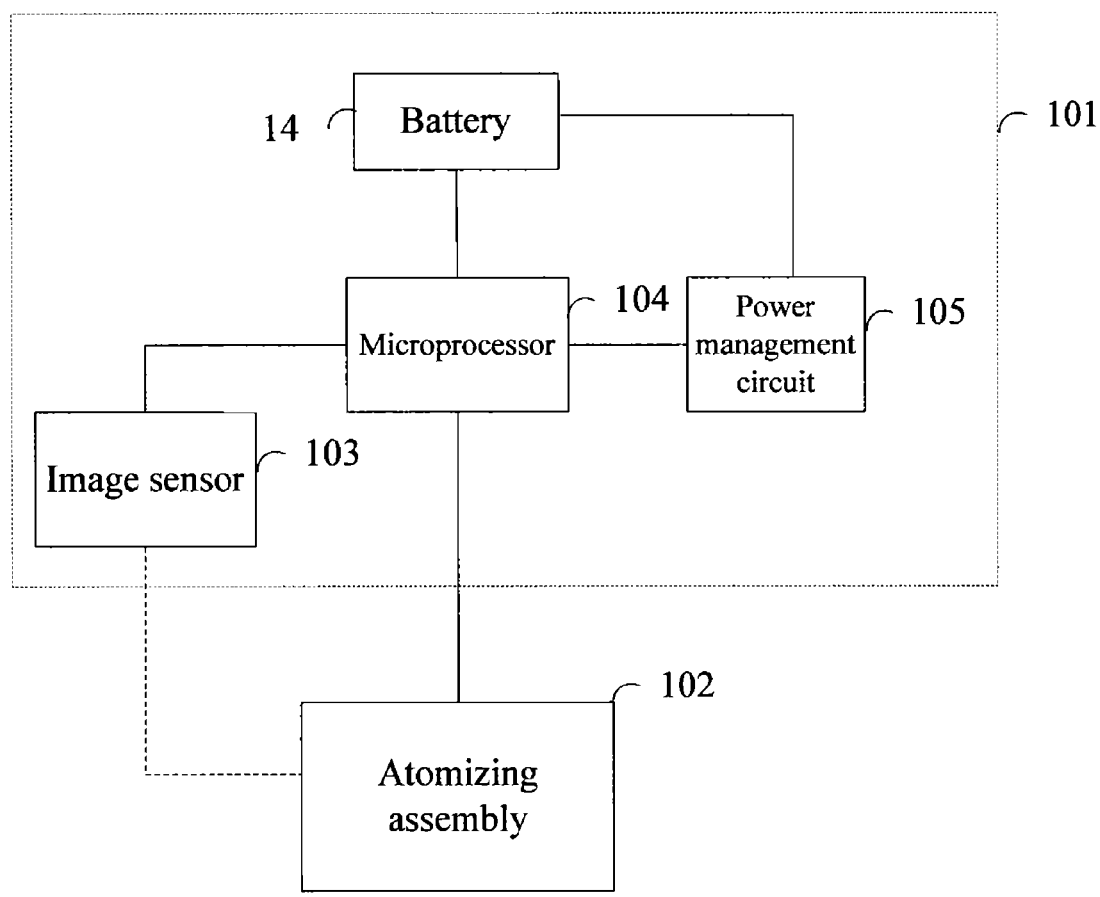
FIG. 3 is a functional block diagram of a battery assembly of an electronic cigarette according to a second embodiment of the present application.

Referring to FIG. 3, based on the first embodiment, the present embodiment provides another battery assembly 101 of an electronic cigarette which is adapted to form an electronic cigarette in combination with an atomizing assembly 102. The battery assembly 101 includes an image identification device for identifying an identifier to be identified which is arranged on an atomizer, and the image identification device includes an image sensor 103, a microprocessor 104 and a power management circuit 105.

The operating principle of the image identification device of the electronic cigarette according to this embodiment is similar to the operating principle of the first embodiment. The image sensor 103 collects the identifier to be identified on the atomizing assembly 102, and sends a collected image to the microprocessor 104. Then, the microprocessor 104 determines whether the identifier to be identified matches with a preset identifier, and when the identifier to be identified matches with the preset identifier, the microprocessor controls a circuit between the battery assembly and the atomizing assembly to turn on, and at this time, the electronic cigarette can work normally. When the identifier to be identified does not match with the preset identifier, the microprocessor controls the circuit between the battery assembly and the atomizing assembly to turn off, and at this time, the electronic cigarette cannot work normally since it is powered off.

Unlike the first embodiment, this embodiment is further provided with the power management circuit 105 arranged between a battery and the microprocessor in the battery assembly to power the microprocessor.

Preferably, in the embodiments, the image sensor 103 may be an infrared image sensor, a photosensitive camera, an ultrasonic imager, a thermal imaging sensor or a magnetic induction imager. More specifically, the image sensor may adopt a scanning imaging manner, for example, an infrared manner of an infrared sensor that is used in a reading pen or barcode scanning. The image sensor may also adopt a photosensitive imaging manner, such as a charge-coupled device (abbreviated as CCD), a digital photography or a digital video. The image sensor may further adopt an ultrasonic imaging manner, for example, an object to be detected is irradiated by ultrasonic waves and reflects the ultrasonic waves into a sensor to form an image. In addition, the image sensor may also adopt a radiation imaging manner, such as thermal imaging, and may also adopt a conductor sensor imaging manner, for example a capacitive sensor, and in this manner, a capacitance of the sensor will change when an object to be detected touches or gets close to the sensor. The image sensor may also adopt a magnetic induction imaging manner, for example, a sensor can sense a shape, a dimension or other information of a magnetic object to be detected when the magnetic object to be detected gets close to or touches the sensor. It is to be noted that, there are various kinds of image sensors, and image sensors may meet the requirement of the present application as long as they can be used for image identification.

Third Embodiment

Figure 4:
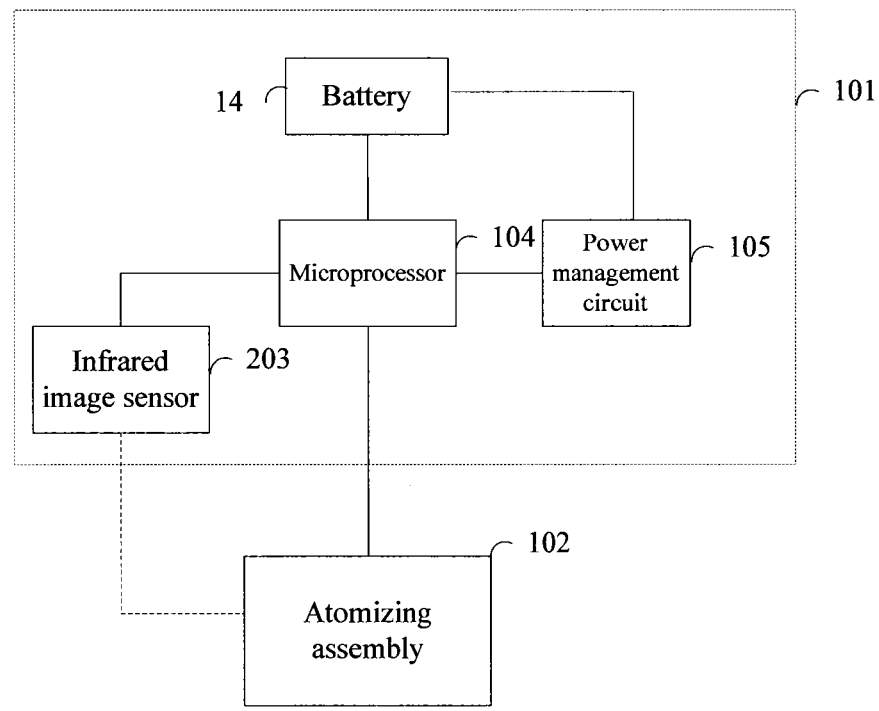
FIG. 4 is a functional block diagram of a battery assembly of an electronic cigarette according to a third embodiment of the present application.

Referring to FIG. 4, the image sensor is an infrared image sensor 203 according to the third embodiment which is a specific implementation of the second embodiment. This embodiment provides a battery assembly 101 of an electronic cigarette which is adapted to form an electronic cigarette in combination with an atomizing assembly 102. The battery assembly 101 includes an image identification device for identifying an identifier to be identified which is arranged on an atomizer, and the image identification device includes an infrared image sensor 203, a microprocessor 104 and a power management circuit 105. Preferably, the infrared image sensor may be an object identifier (OID) code identification chip.

Figure 5:
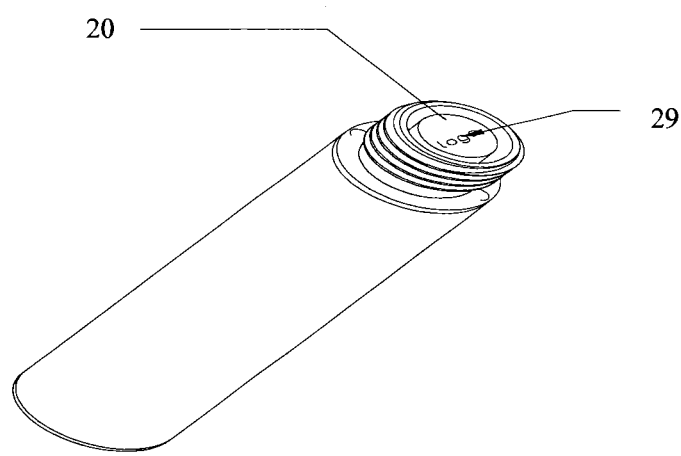
FIG. 5 is a schematic view showing the structure of an atomizing assembly according to the third embodiment of the present application.
Figure 6:
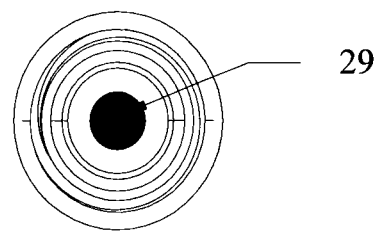
FIG. 6 is a sectional view of the atomizing assembly according to the third embodiment of the present application.

The operating principle of the battery assembly is described as follows. The battery assembly is provided with the infrared image sensor, and the atomizing assembly is provided with a trademark LOGO, and as shown in FIG. 5, an image to be identified 29 is arranged on an end surface (as shown in FIG. 6), close to the battery assembly, of an upper electrode 21 of the atomizing assembly. The trademark is coated with an infrared sensitive material, and when the trademark to be detected is irradiated by infrared light emitted from the sensor, the sensitive material of the trademark may reflect the infrared light, and the infrared image sensor may detect the reflected light to achieve an identification function and then send an identified image to the microprocessor. Then, the microprocessor matches a received image with a preset image. If the microprocessor recognizes the right trademark LOGO, the microprocessor controls the battery assembly to turn on the power supply to the atomizing assembly, so as to power the atomizing assembly, thus the electronic cigarette can work normally. If the trademark LOGO detected by the microprocessor cannot be recognized, that is, it does not match with the preset identifier, the power supply will not be turned on, and the atomizing assembly cannot work, thus the electronic cigarette cannot work normally.

Fourth Embodiment

Figure 7:
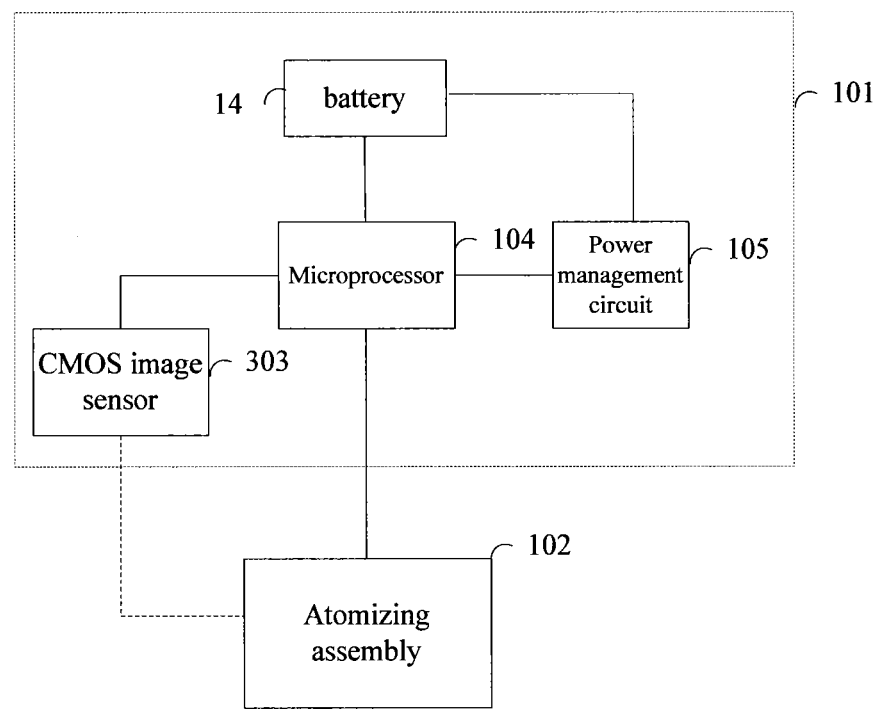
FIG. 7 is a functional block diagram of an electronic cigarette according to a fourth embodiment of the present application.
Figure 8:
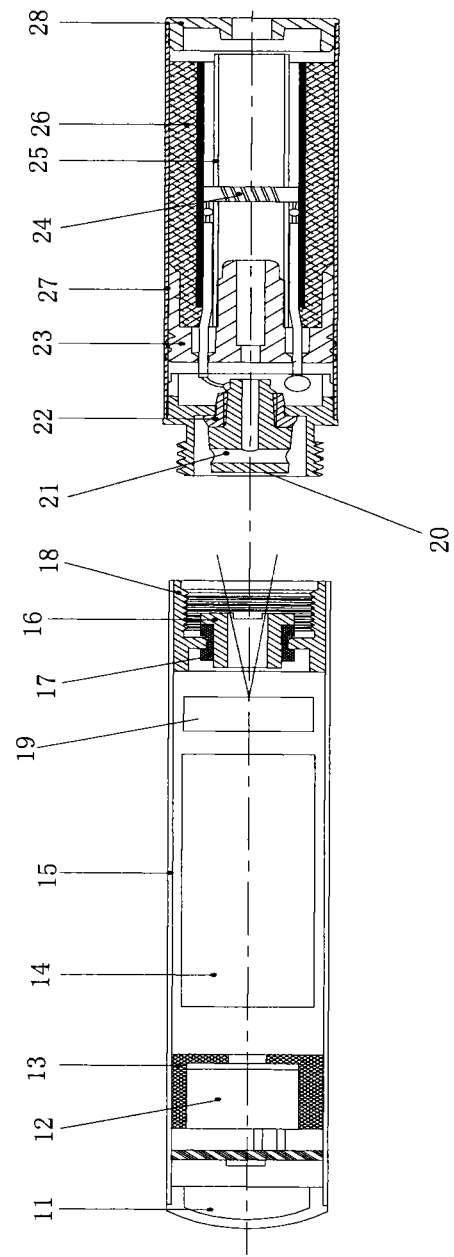
FIG. 8 is a schematic view showing the structure of the electronic cigarette according to the fourth embodiment of the present application.

Referring to FIG. 7, the image sensor is a complementary metal oxide semiconductor (abbreviated as CMOS) image sensor 303 according to the fourth embodiment which is another specific implementation of the second embodiment. A battery assembly 101 of an electronic cigarette according to this embodiment is adapted to form an electronic cigarette in combination with an atomizing assembly 102. The battery assembly 101 includes an image identification device for identifying an identifier to be identified which is arranged on an atomizer, and the image identification device includes an CMOS image sensor 203, a microprocessor 104 and a power management circuit 105. Preferably, the CMOS image sensor may be an SPCA563B image identification chip.

The operating principle of the battery assembly is described as follows. The battery assembly is provided with the CMOS image sensor, and the atomizing assembly is provided with a trademark LOGO. A trademark to be detected is irradiated by near-white light emitted from a light emitting diode (LED) of the CMOS image sensor 19 to form an image in the sensor, and an SPCA563B microprocessor reads a image collected by the CMOS image sensor for analysis and identification. Specifically, the microprocessor matches the received image with a preset image; and if the microprocessor recognizes the right trademark LOGO, the microprocessor controls the battery assembly to turn on the power supply to the atomizing assembly, so as to power the atomizing assembly, thus the electronic cigarette can work normally. And if the trademark LOGO detected by the microprocessor cannot be recognized, that is, it does not match with the preset identifier, the power supply will not be turned on, and the atomizing assembly cannot work, thus the electronic cigarette cannot work normally.

Fifth Embodiment

Figure 9:
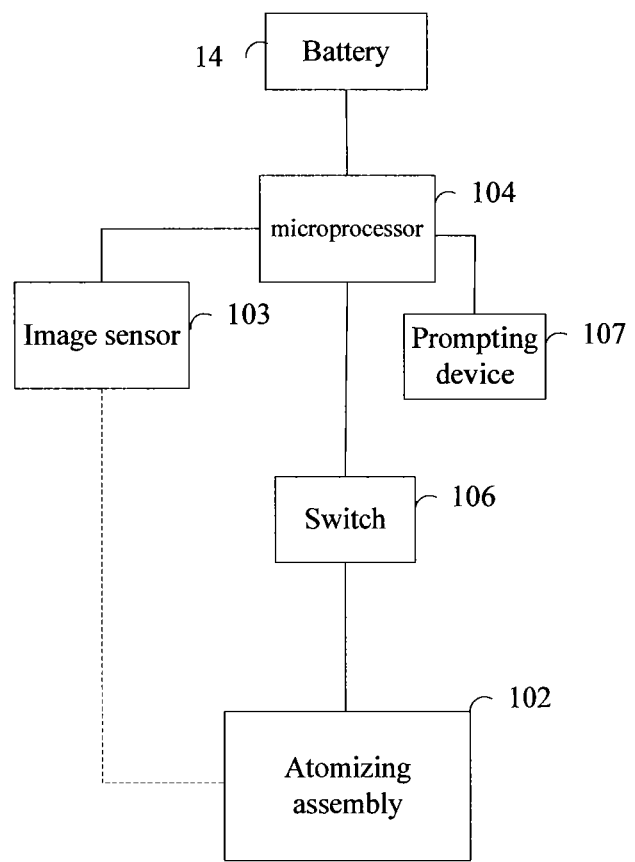
FIG. 9 is a functional block diagram of a battery assembly of an electronic cigarette according to a fifth embodiment of the present application.

Referring to FIG. 9, a battery assembly of an electronic cigarette according to this embodiment is adapted to form an electronic cigarette in combination with an atomizing assembly 102. The battery assembly includes an image identification device for identifying an identifier to be identified which is arranged on an atomizer, and the image identification device includes an image sensor 103, a microprocessor 104 and a switch 106.

The image sensor 103 collects the identifier to be identified on the atomizing assembly 102, and sends the collected image to the microprocessor 104. Then, the microprocessor 104 determines whether the identifier to be identified matches with a preset identifier, and if the identifier to be identified matches with the preset identifier, the microprocessor controls a circuit between the battery assembly and the atomizing assembly to turn on, and at this time, the switch 106 is pressed down and the electronic cigarette can work normally; and if the identifier to be identified does not match with the preset identifier, the microprocessor controls the circuit between the battery assembly and the atomizing assembly to turn off, and at this time, the electronic cigarette can not work normally since it is powered off.

It is to be noted that, the switch 106 may be a pneumatic sensor switch, and may also be a mechanical key switch. Preferably, this embodiment further provides a prompting device electrically connected to the microprocessor and used to prompt an identification result from the microprocessor. The prompting device may be an alarm or an indicator light, and the alarm may be a buzzer alarm, a loudspeaker or the like.

Sixth Embodiment

In addition to the above embodiments, this embodiment further provides an atomizing assembly of an electronic cigarette, wherein an identifier to be identified is arranged on an end surface, close to a battery assembly, of an upper electrode of the atomizing assembly. In this embodiment, the upper electrode is provided with an outer electrode and an inner electrode which are sleevedly engaged, and the identifier to be identified is arranged on the inner electrode.

As can be seen from this embodiment, an electronic cigarette may be formed by combining an atomizing assembly with a battery assembly. Therefore, this embodiment further provides an electronic cigarette including a battery assembly and an atomizing assembly, wherein the battery assembly includes the image identification device described in any one of the above embodiments, and an identifier to be identified is arranged on an end surface, close to the battery assembly, of an upper electrode of the atomizing assembly.

A battery assembly of an electronic cigarette according to the present application is adapted to form an electronic cigarette in combination with an atomizing assembly. The image identification device includes an image sensor and a microprocessor. The microprocessor matches an identifier to be identified collected by the image sensor with a preset identifier, and if the identifier to be identified matches with the preset identifier, the microprocessor controls a circuit between the battery assembly and the atomizing assembly to turn on, thus the electronic cigarette can work normally. That is, the electronic cigarette has an identification function that it can be normally used only when the battery assembly and the atomizing assembly of the electronic cigarette are matched, thereby avoiding damage to the connectors of the electronic cigarette caused by mismatching. In addition, the present application may further avoid the user having a poor experience due to use of the conventional battery assembly and atomizing assembly in any combination, mixed use of tobacco tars having different flavors, and mixed use of the battery assembly and the atomizing assembly from different manufacturers. Thus, the present application may facilitate the recognition of the user of the manufactures and brands, and is more beneficial for the user to quit smoking.

The above embodiments are described in a progressive manner. Each of the embodiments is mainly focused on describing its differences from other embodiments, and references may be made among these embodiments with respect to the same or similar portions among these embodiments. For the device in the embodiments, the description thereof is relatively simpler since it is corresponding to the method disclosed in the embodiments, hence, related parts of the device can refer to the description of the method.

Based on the above description of the disclosed embodiments, the person skilled in the art is capable of carrying out or using the present application. It is obvious for the person skilled in the art to make many modifications to these embodiments. The general principle defined herein may be applied to other embodiments without departing from the spirit or scope of the present application. Therefore, the present application is not limited to the embodiments illustrated herein, but should be defined by the broadest scope consistent with the principle and novel features disclosed herein.

REFERENCE NUMERALS IN FIGS. 1 TO 9

11 end cap,
12 microphone controller,
13 microphone seat,
14 battery,
15 battery sleeve,
16 lower electrode,
17 electrode fixing seat,
18 connecting seat,
19 sensor,
20 connector,
21 upper electrode,
22 upper insulating ring,
23 atomizing seat,
24 atomizing device,
25 PVC fiberglass sleeving,
26 tar storage cotton,
27 atomizing sleeve,
28 mouthpiece cover,
29 identifier to be identified (for example a trademark or a LOGO);
101 battery assembly,
102 atomizing assembly,
103 image sensor,
104 microcontroller
105 power management circuit,
203 infrared image sensor, and
303 CMOS image sensor.

The invention claimed is:

1. An electronic cigarette comprising: a battery assembly and an atomizing assembly, wherein the battery assembly comprises an image identification device configured to identify an identifier to be identified which is arranged on the atomizing assembly, and the image identification device comprises an image sensor and a microprocessor,
wherein the image sensor is configured to collect the identifier to be identified and send a collected image to the microprocessor; and the microprocessor is connected to the image sensor, and in a case that the microprocessor determines that the identifier to be identified matches with a preset identifier, the microprocessor is configured to control a circuit between the battery assembly and the atomizing assembly to turn on so as to enable the electronic cigarette to work normally, and
wherein the image sensor is a magnetic induction Imager.

2. This electronic cigarette according to claim 1, wherein the image sensor is an OID code identification chip or an SPCA563B image identification chip.

3. This electronic cigarette according to claim 1, further comprising:
a power management circuit arranged between a battery and the microprocessor in the battery assembly and configured to manage an external power supply to charge the battery.

4. This electronic cigarette according to claim 1, further comprising:
a prompting device electrically connected to the microprocessor and configured to display an identification result from the microprocessor, wherein the prompting device is an alarm or an indicator light.

5. The electronic cigarette according to claim 1, wherein the identifier to be identified by the battery assembly is arranged on a portion, close to the battery assembly, of the atomizing assembly.

6. The electronic cigarette according to claim 1, wherein the identifier to be identified is a trademark of the electronic cigarette.

7. The electronic cigarette according to claim 1, wherein the identifier to be identified is a pattern or a text of a planar or a three-dimensional shape.

8. The electronic cigarette according to claim 1, wherein the atomizing assembly is provided with an upper electrode adapted to electrically connect to the battery assembly, the upper electrode is provided with an outer electrode and an inner electrode which are sleevedly engaged, and the identifier to be identified is arranged on the inner electrode.

* * * * *